United States Patent [19]

Doherty et al.

[11] 4,247,416
[45] Jan. 27, 1981

[54] CRYSTALLINE ZEOLITE ZSM-25

[75] Inventors: Harry G. Doherty, Pitman; Charles J. Plank, Woodbury; Edward J. Rosinski, Pedricktown, all of N.J.

[73] Assignee: Mobil Oil Corporation, Fairfax, Va.

[21] Appl. No.: 16,248

[22] Filed: Feb. 28, 1979

[51] Int. Cl.³ .................... C01B 33/28; B01J 31/14
[52] U.S. Cl. .................. 252/428; 252/431 N; 252/455 Z; 260/448 C; 423/328; 423/329
[58] Field of Search .................. 423/328–330; 260/448 C; 252/431 N, 455 Z

[56] References Cited

U.S. PATENT DOCUMENTS

| | | | |
|---|---|---|---|
| 3,012,853 | 12/1961 | Milton | 423/328 |
| 3,306,922 | 2/1967 | Barrer et al. | 260/448 C |
| 3,709,979 | 1/1973 | Chu | 423/328 |
| 3,832,449 | 8/1974 | Rosinski et al. | 423/328 |
| 3,972,983 | 8/1976 | Ciric | 423/328 |

Primary Examiner—Edward J. Meros
Attorney, Agent, or Firm—Charles A. Huggett; Charles J. Speciale

[57] ABSTRACT

A new crystalline zeolite, designated "ZSM-25", a method of making the zeolite and using the zeolite in catalytic conversion of hydrocarbons, is the subject of this application. The new zeolite has a composition in the anhydrous state expressed in terms of mole ratios of oxides as follows:

$$(0.01-0.4)R_2O:(0.9\pm0.2)M_2O:Al_2O_3: (6-10)SiO_2$$

wherein R is an organic nitrogen-containing cation such as tetraethylammonium ions and M is an alkali metal cation such as sodium and is characterized by a specified X-ray powder diffraction pattern.

14 Claims, 2 Drawing Figures

X-RAY DIFFRACTION PATTERN OF ZSM-25
PRODUCT OF EXAMPLE I

FIG. 1  X-RAY DIFFRACTION PATTERN OF ZSM-25 PRODUCT OF EXAMPLE I

X-RAY DIFFRACTION PATTERN OF ZSM-25 SAMPLE CALCINED FOUR HOURS AT 500°C

CRYSTALLINE ZEOLITE ZSM-25

BACKGROUND OF THE INVENTION

1. Field of the Invention

This invention relates to a novel synthetic crystalline zeolite and to methods for its preparation. More particularly, this invention relates to a novel synthetic crystalline aluminosilicate having catalytic properties, to methods for preparing the same, and to hydrocarbon conversion therewith.

2. Description of the Prior Art

Zeolitic materials, both natural and synthetic, have been demonstrated in the past to have catalytic capabilities for various types of hydrocarbon conversion. Certain zeolitic materials are ordered, porous crystalline aluminosilicates having a definite crystalline structure within which there are a large number of small cavities which are interconnected by a number of still smaller cavities. These cavities and channels are uniform in size. Since the dimensions of these pores are such as to accept for absorption molecules of certain dimensions while rejecting those of larger dimensions, these materials have come to be known as "molecular sieves" and are utilized in a variety of ways to take advantage of these properties.

Such molecular sieves include a wide variety of positive ion-containing crystalline aluminosilicates, both natural and synthetic. These aluminosilicates can be described as a rigid three-dimensional network of $SiO_4$ and $AlO_4$ in which the tetrahedra are cross-linked by the sharing of oxygen atoms whereby the ratio of the total aluminum and silicon atoms to oxygen is 1:2. The electrovalence of the tetrahedra-containing aluminum is balanced by the inclusion in the crystal of a cation, for example, an alkali metal or an alkaline earth metal cation. This can be expressed by a formula wherein the ratio of Al to the number of the various cations, such as $Ca/2$, $Sr/2$, $Na$, $K$ or $Li$, is equal to unity. One type of cation has been exchanged either in entirety or partially by another type of cation utilizing ion exchange techniques in a conventional manner. By means of such cation exchange it has been possible to vary the size of the pores in the given aluminosilicate by a suitable selection of the particular cation. The spaces between the tetrahedra are occupied by molecules of water prior to dehydration.

Prior art techniques have resulted in the formation of a great variety of synthetic crystalline aluminosilicates. These aluminosilicates have come to be designated by letter or other convenient symbol, as illustrated by zeolite A (U.S. Pat. No. 2,882,243), zeolite X (U.S. Pat. No. 2,882,244), zeolite Y (U.S. Pat. No. 3,130,007), zeolite K-G (U.S. Pat. No. 3,055,654), zeolite ZK-5 (U.S. Pat. No. 3,247,195), zeolite β (U.S. Pat. No. 3,308,069), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), and zeolite ZSM-35 (U.S. Pat. No. 4,016,245).

SUMMARY OF THE INVENTION

This invention is directed to a synthetic crystalline aluminosilicate, hereinafter designated "Zeolite ZSM-25" or simply "ZSM-25," to methods for its preparation, and to hydrocarbon conversion processes therewith. The ZSM-25 composition can be identified in terms of mole ratios of oxides in the anhydrous state as follows:

$$(0.01-0.4)R_2O:(0.9\pm0.2)M_2O:Al_2O_3:(6-10)SiO_2$$

wherein R is an organic nitrogen-containing cation containing at least one alkyl or aryl group having between 1 and 7 carbon atoms, preferably between 2 and 5 carbon atoms, more preferably containing at least one ethyl group, and still more preferably R is a quaternary ammonium cation containing at least one ethyl group, and M is an alkali metal cation, especially sodium.

The original cations can be replaced in accordance with techniques well known at least in part by ion exchange with other cations. Preferred replacing cations include metal ions, ammonium ions, hydrogen ions, and mixtures of the same. Particularly preferred cations are those which render the zeolite catalytically active, especially for hydrocarbon conversion. These include hydrogen, rare earth metals, aluminum, metals of Groups II and VIII of the Periodic Table, and manganese.

ZSM-25 zeolites posses a definite distinguishing crystalline structure whose X-ray diffraction pattern shows the following significant lines as given in TABLE I below:

TABLE I

MOST SIGNIFICANT LINES

| $2\theta$ | $d(A)$ | Relative Intensity | $2\theta$ | $d$ | Relative Intensity |
|---|---|---|---|---|---|
| 9.94 | 8.90 ± .18 | W | 22.60 | 3.93 ± .08 | W |
| 11.00 | 8.04 ± .16 | VS | 24.12 | 3.69 ± .08 | S |
| 12.05 | 7.34 ± .15 | W | 26.61 | 3.35 ± .07 | M |
| 12.63 | 7.01 ± .14 | VS | 26.89 | 3.32 ± .07 | VS |
| 13.79 | 6.42 ± .13 | S | 27.47 | 3.25 ± .07 | VS |
| 14.62 | 6.06 ± .12 | M | 28.33 | 3.15 ± .06 | M |
| 15.40 | 5.75 ± .12 | M | 28.74 | 3.11 ± .06 | VS |
| 15.70 | 5.64 ± .12 | M | 29.44 | 3.03 ± .06 | S |
| 16.83 | 5.27 ± .11 | M | 30.74 | 2.91 ± .06 | W |
| 17.31 | 5.12 ± .11 | W | 31.85 | 2.81 ± .06 | M |
| 17.73 | 5.00 ± .10 | M | 32.93 | 2.72 ± .06 | M |
| 19.24 | 4.61 ± .09 | VS | 34.00 | 2.64 ± .05 | M |
| 19.62 | 4.52 ± .09 | M | 40.07 | 2.25 ± .05 | W |
| 21.72 | 4.09 ± .08 | M | 44.24 | 2.05 ± .04 | W |

These values were determined by standard techniques. The radiation was the K-alpha doublet of copper, and a scintillation counter spectrometer with a strip chart pen recorder was used. The peak heights, I, and the positions as a function of 2 times theta ($2\theta$), where theta is the Bragg angle, were read with the spectrometer chart. From these, the relative intensities, $I/I_o$, where $I_o$ is the intensity of the strongest line or peak, and d is the interplanar spacing in Angstroms (A), corresponding to the recorded lines, were calculated. The relative intensity in the table above is expressed as follows:

| Relative Intensity | 100 $I/I_o$ |
|---|---|
| VS (Very Strong) | 60–100 |
| S (Strong) | 40–60 |
| M (Medium) | 20–40 |
| W (Weak) | 0–20 |

It should be understood that this X-ray diffraction pattern is characteristic of all the species of ZSM-25 compositions. Ion exchange of the sodium ion with cations reveals substantially the same pattern with some minor shifts in interplanar spacing and variation in relative intensity. Other minor variations can occur, depending on the silicon to aluminum ratio of the particular sample as well as if it has been subjected to thermal treatment.

The ZSM-25 zeolite is useful as an absorbent and is active in a broad area of hydrocarbon conversion reactions. In particular, the ZSM-25 zeolite is useful in the processes of polymerization, including oligomerization and isomerization. The ZSM-25 zeolite as indicated above is also useful in other catalytic processes such as catalytic cracking of hydrocarbons and hydrocracking. The ZSM-25 zeolite is thermally stable under the conditions required for catalytic cracking of hydrocarbons and provides conversion of the cracked oil to materials having lower molecular weights and boiling points which are of greater economic value. The ability to be physically stable under high temperatures and/or in the presence of high temperature steam is extremely important for a cracking catalyst. During catalytic conversion, the reaction which takes place is essentially a cracking to produce hydrocarbons. However, this cracking is accompanied by a number of complex side reactions such as aromatization, polymerization, alkylation, and the like. As a result of these complex reactions, a carbonaceous deposit is laid down on the catalyst which is referred to by petroleum engineers as "coke". The deposit of coke on the catalyst tends to seriously impair the catalyst efficiency for the principle reaction desired and to substantially decrease the rate of conversion and/or the selectivity of the process. Thus, it is common to remove the catalyst after coke has been deposited thereon and to regenerate it by burning the coke in a stream of oxidizing gas. The regenerated catalyst is returned to the conversion stage of the process cycle. The enhanced thermal stability of ZSM-25 is advantageous in this regard.

ZSM-25 can be used either in the alkali metal form, e.g., the sodium form, the ammonium form, the hydrogen form, or another univalent or multivalent cationic form. The zeolite can also be used in intimate combination with a hydrogenating component such as tungsten, vanadium, molybdenum, rhenium, nickel, cobalt, chromium, magnesium, or a noble metal, such as platinum or palladium where a hydrogenation dehydrogenation function is to be performed. Such components can be exchanged into the composition, impregnated therein or physically intimately admixed therewith. Such components can be impregnated in or onto ZSM-25, such as, for example, by, in the case of platinum, treating the zeolite with a platinum metal-containing ion. Thus, suitable platinum compounds for this purpose include chloroplatinic acid, platinuous chloride and various compounds containing the platinum amine complex. Combinations of metals and methods for their introduction can also be used.

The compounds of the useful platinum or other metals can be divided into compounds in which the metal is present in the cation of the compound and compounds in which it is present in the anion of the compound. Both types of compounds which contain the metal in the ionic state can be used. A solution in which platinum metals are in the form of a cation or cationic complex, e.g., $Pt(NH_3)_6Cl_4$, is particularly useful. For some hydrocarbon conversion processes this noble metal form of the ZSM-25 catalyst is unnecessary, such as in low temperature, liquid phase orthoxylene isomerization.

In the ZSM-25 zeolite R is an organic nitrogen containing a cation such as a tetraethylammonium ion. A specific example of a suitable tetraethylammonium salt as the source of this ion is tetraethylammonium bromide. Other suitable salts as sources of the tetraethylammonium ion are tetraethylammonium chloride, tetraethylammonium solids, and tetraethylammonium sulfate as well as the hydroxides.

In the ZSM-25 zeolite, M can be one or more of a variety of alkali metal cations, suitably defined as including all alkali metal ions derived from alkali metal oxide or hydroxide as well as alkali metal ions included in alkali metal silicates and aluminates (not including alkali metal salts such as sodium chloride or sodium sulfate which may be derived from neutralization of added inorganic acids such as HCl or $H_2SO_4$ or acid salts such as $Al_2(SO_4)_3$). Nonlimiting examples of such suitable alkali metal ions include sodium and potassium.

The ZSM-25 zeolite when employed either as an adsorbent or as a catalyst in a hydrocarbon conversion process should be dehydrated at least partially. This can be done by heating to a temperature in the range of 200° to 600° C. in an atmosphere such as air, nitrogen, steam, etc. and at atmospheric or subatmospheric pressures for a time between 1 and 48 hours. Dehydration can also be performed at lower temperature merely by placing a catalyst in a vacuum but a longer time is required to obtain a sufficient amount of dehydration.

Zeolite ZSM-25 can be suitably prepared by preparing a solution containing sources of tetraethylammonium cations, sodium oxide, an oxide of aluminum, an oxide of silicon, and water having a composition in terms of mole ratios of oxides, falling within the ranges indicated below:

|  |  | Preferred |
| --- | --- | --- |
| $SiO_2/Al_2O_3$ | 5–15 | 8–10 |
| $R^+/R^+ + M^+$ | 0.4–1.0 | 0.6–0.8 |
| $OH^-/SiO_2$ | 0.3–0.7 | 0.4–0.6 |
| $H_2O/OH^-$ | 50–300 | 60–150 | where R and M are as defined above and maintaining the mixture until crystals of the zeolite are formed. Thereafter, the crystals are separated from the liquid and recovered. Typical reaction conditions consist of heating the foregoing reaction mixture to a temperature of from about 80° C. to 180° C. at a pressure within the range of about 75 psig to 200 psig for a period of time of from about six hours to 150 days. A more preferred temperature range is from about 121° C. to 149° C. at a pressure within the range of 100 to 175 psig for a time period of about four days.

The digestion of the gel particles is carried out until crystals form. The time required under these conditions is about four days. The solid product is separated from the reaction medium as by cooling the whole to room temperature, filtering and water washing.

ZSM-25 may be synthesized from a mixture containing colloidal silica, sodium aluminate, sodium hydroxide, tetraethylammonium compounds, and water at a crystallization temperature of 135° C., at a pressure of 100-175 psig. The product is dried, e.g., at 110° C. for from about 16 to 24 hours. Milder conditions may be employed if desired, such as at room temperature under vacuum.

ZSM-25 is preferably formed as an aluminosilicate. The composition can be prepared utilizing materials which supply the appropriate oxide. Such compositions include for an aluminosilicate, sodium aluminate, colloidal silica, sodium hydroxide, and tetraethylammonium compounds such as tetraethylammonium bromide. Each oxide component utilized in the reaction mixture for preparing ZSM-25 can be supplied by one or more initial reactants and they can be mixed together in any order. For example, sodium oxide can be prepared by an aqueous solution of sodium hydroxide or by an aqueous solution of sodium silicate; tetraethylammonium cation can be supplied by tetraethylammonium hydroxide, tetraethylammonium bromide, or tetraethylammonium chloride or tetraethylammonium sulfate. The reaction mixture can be prepared either batchwise or continuously. Crystal size and crystallization time of the ZSM-25 composition will vary with the nature of the reaction mixture employed.

DESCRIPTION OF SPECIFIC EMBODIMENTS

Figure 1:
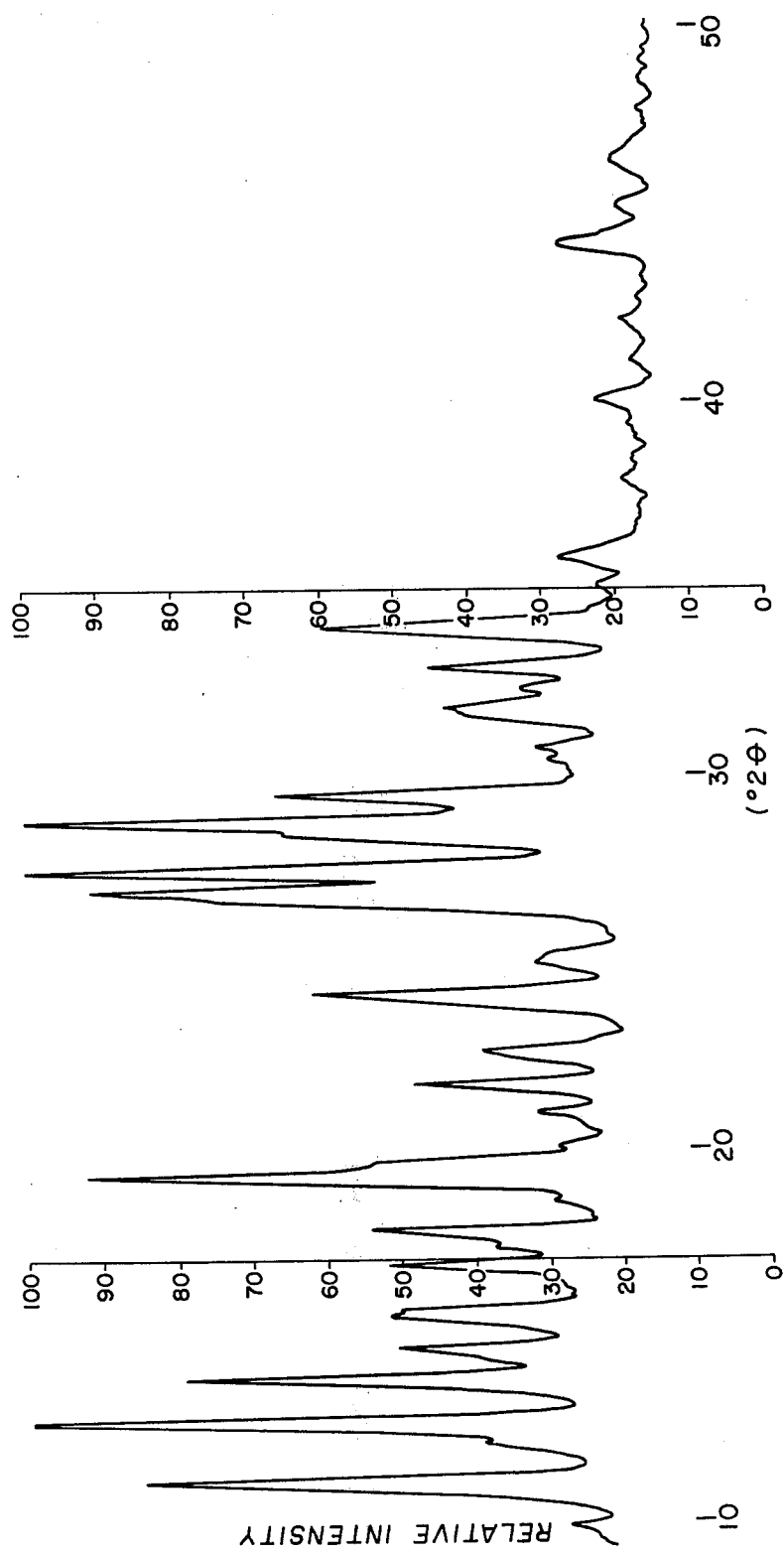
FIG. 1 is an X-ray diffraction pattern of the ZSM-25 product of Example I.

ZSM-25 zeolites can have the original cations associated therewith replaced by a wide variety of other cations according to techniques well known in the art. Typical cations would include hydrogen, ammonium, and metal cations, including mixtures of the same. Of the replacing metallic cations, particular preference is given to cations of metals such as rare earth metals, magnesium, calcium, as well as metals of Group II of the Periodic Table, e.g., zinc, and Group VIII of the Periodic Table, e.g., nickel. Because of pore blockage by the organic cation it may be desirable to subject the zeolite to a thermal treatment prior to carrying out the ion exchange. Such a thermal treatment may be carried out in the presence of an atmosphere of, for example, air, steam, nitrogen, hydrogen and oxygen at a temperature within the range of about 400° C. to 900° C.

Representative ionic exchange techniques are disclosed in a wide variety of patents, including U.S. Pat. Nos. 3,140,249, 3,140,251, and 3,140,253.

Following contact with the salt solution of the desired replacing cation, the zeolites are then preferably washed with water and dehydrated at a temperature ranging from 150° F. to 1500° F. for periods of time ranging from 1 to 48 hours or more.

Regardless of the cations replacing the sodium in the synthesized form of the ZSM-25, the spatial arrangement of the aluminum, silicon, and oxygen atoms which form the basic crystal lattice of ZSM-25, remains essentially unchanged by the desired replacement of sodium or other alkali metal as determined by taking an X-ray powder diffraction pattern of the ion-exchanged material. Such X-ray diffraction pattern of the ion-exchanged ZSM-25 reveals a pattern substantially the same as that set forth in TABLE I above.

The aluminosilicates prepared by the instant invention are formed in a wide variety of particle sizes. Generally speaking, the particles can be in the form of a powder, a granule, or molded product, such as extrudate having particle size sufficient to pass through a 2-mesh (Tyler) screen and be retained on a 400-mesh (Tyler) screen. In cases where the catalyst is molded, such as by extrusion, the aluminosilicate can be extruded before drying or dried or partially dried and then extruded.

In the case of many catalysts, it is desired to incorporate the ZSM-25 with a matrix material resistant to the temperatures and other conditions employed in organic conversion processes. Such materials include active and inactive material and synthetic or naturally occurring zeolites as well as inorganic materials such as clays, silica and/or metal oxides. The latter may be either naturally occurring or in the form of gelatinous precipitates or gels including mixtures of silica and metal oxides. Use of a material in conjunction with the ZSM-25, i.e., combined therewith which is active, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. Commonly, zeolite materials have been incorporated into naturally occurring clays, e.g., bentonite and kaolin, to improve the crushing strength of the catalyst under commercial operating conditions. These materials, i.e., clays, oxides, etc., function as binders for the catalyst. It is desirable to provide a catalyst having good crush strength, because in a petroleum refinery the catalyst is often subjected to rough handling which tends to break the catalyst down into powder-like materials which cause problems in processing. These clay binders have been employed for the purpose of improving the crush strength of the catalyst.

Naturally occurring clays which can be composited with the ZSM-25 catalyst include the montmorillonite and kaolin family, which families include the sub-bentonites and the kaolins commonly known as the Dixie McNamee-Georgia and Florida clays or others in which the main mineral constituent is halloysite, kaolinite, dickite, nacrite, and anauxite. Such clays can be used in the raw state as originally mined or initially subjected to calcination, acid treatment or chemical modification.

In addition to the foregoing materials, the ZSM-25 catalyst can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia. The matrix can be in the form of a cogel. The relative proportions of finely divided crystalline aluminosilicate ZSM-25 and organic oxide gel matrix vary widely with the crystalline aluminosilicate content ranging from about 1 to about 90 percent by weight and usually, particularly when the composition is prepared in the form of beads, in the range of about 2 to about 50 percent by weight of the composite.

Employing the ZSM-25 catalyst of this invention containing a hydrogenation component, heavy petroleum residual stocks, cycle stocks and other hydrocrackable charge stocks can be hydrocracked at temperatures between 400° F. and 825° F. using molar ratios of hydrogen to hydrocarbon charge in the range of 2 to 80. The pressure employed will vary between 10 and 2,500 psig and the liquid hourly space velocity between 0.1 and 10.

Employing the catalyst of this invention for catalytic cracking, hydrocarbon cracking stocks can be cracked at a liquid hourly space velocity between about 0.5 and 50, a temperature between about 550° F. and 1100° F., a pressure between about subatmospheric and several hundred atmospheres.

Employing a catalytically active form of the ZSM-25 zeolite of this invention containing a hydrogenation component, reforming stocks can be reformed employing a temperature between 700° and 1000° F. The pressure can be between 100 and 1000 psig but is preferably between 200 and 700 psig. The liquid hourly space velocity is generally between 0.1 and 10, preferably between 0.5 and 4 and the hydrogen to hydrocarbon mole ratio is generally between 1 and 20, preferably between 4 and 12.

The catalyst can also be used for hydroisomerization of normal paraffins, when provided with a hydrogenation component, e.g., platinum. Hydroisomerization is carried out at a temperature between 200° and 700° F., preferably 300° F. and 550° F. and with a liquid hourly space velocity between 0.01 and 2, preferably between 0.25 and 0.50 employing hydrogen such that the hydrogen to hydrocarbon mole ratio is between 1:1 and 5:1. Additionally, the catalyst can be used for olefin and aromatic isomerization employing temperatures between 30° F. and 900° F., preferably 150° F. to about 600° F.

The catalyst can also be used for the oligomerization (polymerization) of olefins at a temperature of about 500° F. to about 900° F. and a liquid hourly space velocity of about 0.1 to about 10.

The catalyst can also be used for reducing the pour point of gas oils. This reduction is carried out at a liquid hourly space velocity between about 1 and about 30 and at a temperature between about 800° F. and about 1100° F.

Other reactions which can be accomplished employing the catalyst of this invention containing a metal, e.g., platinum, include hydrogenation-dehydrogenation reactions and desulfurizations.

In order to more fully illustrate the nature of the invention and the manner of practicing the same, the following examples are presented.

In the examples which follow, whenever adsorption data is set forth it was determined as follows:

A weighted sample of the zeolite was contacted with the desired pure adsorbent vapor in an adsorption chamber at a pressure less than the vapor-liquid equilibrium pressure of the adsorbent at room temperature. This pressure was kept constant during the adsorption period which did not exceed about eight hours. Adsorption was complete when a constant pressure in the adsorption chamber was reached, i.e., 12 mm of mercury for water and 20 mm for n-Hexane and cyclohexane. The increase in weight was calculated as the adsorption capacity of the sample.

EXAMPLE I

A ZSM-25 zeolite was synthesized from a mixture containing 228.0 grams colloidal silica (30% $SiO_2$), 30.0 grams $NaAlO_2$, 8.7 grams sodium hydroxide (NaOH), 330.0 grams tetraethylammonium bromide (($CH_3CH_2$)$_4$NBr) and 282 grams water ($H_2O$).

The resulting mixture had the following molar composition expressed in terms of mole ratios.

| | |
|---|---|
| $SiO_2/Al_2O_3$ | 9.0 |
| $R^+/R^+ + M^+$ | 0.75 |
| $OH^-/SiO_2$ | 0.47 |
| $H_2O/OH^-$ | 101 |

The pH of this composition ranges from about 13.7 to 14.7.

Crystallization was carried out in a glass-lined, stirring autoclave at 275° F. and a pressure of 100–175 psig. The time for crystallization was four days. The resulting solid product was cooled to room temperature, removed, filtered, washed with water and dried at 230° F.

Chemical analysis of the product dried at 230° F. showed the formula to be:

$$(0.12)R_2O:(0.87)Na_2O:Al_2O_3:(8.5)SiO_2$$

where R is a tetraethylammonium ion. The product contained 3.8% by weight carbon and 0.5% by weight nitrogen.

By varying the starting composition for the zeolite, as previously indicated, products can be obtained as indicated by the formula below:

$$(0.01-0.4)R_2O:(0.9\pm0.2)Na_2O:Al_2O_3:(6-10)SiO_2$$

A portion of the noncalcined product was subjected to X-ray analysis and identified as ZSM-25. The material exhibited the X-ray powder diffraction pattern as shown in FIG. 1 and TABLE II.

TABLE II

X-RAY DATA ZSM-25 NONCALCINED

| 2θ | d | Relative Intensity | 2θ | d | Relative Intensity |
|---|---|---|---|---|---|
| 5.50 | 16.06 | 2 | 33.61 | 2.666 | 9 |
| 7.20 | 12.28 | 2 | 33.98 | 2.638 | 40 |
| 7.60 | 11.63 | 2 | 34.46 | 2.603 | 4 |
| 8.23 | 10.74 | 2 | 35.10 | 2.557 | 4 |
| 9.56 | 9.25 | 4 | 35.82 | 2.507 | 10 |
| 9.90 | 8.93 | 7 | 36.13 | 2.486 | 3 |
| 10.95 | 8.08 | 67 | 37.55 | 2.395 | 2 |
| 12.00 | 7.37 | 13 | 37.90 | 2.374 | 4 |
| 12.58 | 7.04 | 86 | 38.33 | 2.348 | 3 |
| 13.74 | 6.44 | 56 | 38.67 | 2.328 | 2 |
| 14.25 | 6.22 | 5 | 39.04 | 2.307 | 2 |
| 14.58 | 6.08 | 25 | 39.47 | 2.283 | 3 |
| 15.39 | 5.76 | 20 | 40.03 | 2.252 | 7 |
| 15.61 | 5.68 | 20 | 40.87 | 2.208 | 2 |
| 16.13 | 5.49 | 2 | 41.16 | 2.193 | 2 |
| 16.80 | 5.28 | 30 | 41.56 | 2.173 | 1 |
| 17.27 | 5.13 | 14 | 41.91 | 2.156 | 2 |
| 17.70 | 5.01 | 34 | 42.22 | 2.140 | 4 |
| 18.51 | 4.79 | 6 | 42.70 | 2.118 | 1 |
| 19.19 | 4.62 | 72 | 43.40 | 2.085 | 1 |
| 19.56 | 4.54 | 26 | 43.62 | 2.075 | 1 |
| 19.99 | 4.44 | 6 | 44.19 | 2.050 | 12 |
| 20.55 | 4.32 | 3 | 44.56 | 2.033 | 3 |
| 20.93 | 4.24 | 12 | 45.08 | 2.011 | 2 |
| 21.66 | 4.10 | 29 | 45.32 | 2.001 | 5 |
| 22.34 | 3.98 | 8 | 46.20 | 1.965 | 3 |
| 22.54 | 3.94 | 15 | 46.48 | 1.954 | 4 |
| 23.77 | 3.74 | 11 | 46.68 | 1.946 | 4 |
| 24.07 | 3.70 | 44 | 47.05 | 1.931 | 2 |
| 24.85 | 3.58 | 8 | 47.83 | 1.902 | 3 |
| 25.15 | 3.54 | 9 | 48.63 | 1.872 | 1 |
| 26.56 | 3.36 | 22 | 49.17 | 1.853 | 2 |
| 26.83 | 3.32 | 67 | 50.63 | 1.803 | 1 |
| 27.42 | 3.25 | 100 | 51.50 | 1.774 | 35 |
| 28.30 | 3.15 | 34 | 52.08 | 1.756 | 3 |
| 28.68 | 3.11 | 80 | 52.68 | 1.737 | 7 |
| 29.38 | 3.04 | 50 | 54.15 | 1.694 | 5 |
| 29.97 | 2.981 | 3 | 54.38 | 1.687 | 6 |
| 30.35 | 2.945 | 8 | 54.85 | 1.674 | 6 |
| 30.74 | 2.909 | 12 | 55.69 | 1.650 | 2 |
| 31.52 | 2.838 | 11 | 56.56 | 1.627 | 5 |
| 31.80 | 2.814 | 22 | 57.11 | 1.613 | 3 |
| 32.30 | 2.772 | 13 | 58.10 | 1.588 | 5 |
| 32.87 | 2.725 | 28 | 58.98 | 1.566 | 3 |

TABLE II-continued

| X-RAY DATA ZSM-25 NONCALCINED | | | | | |
|---|---|---|---|---|---|
| 2θ | d | Relative Intensity | 2θ | d | Relative Intensity |
| | | | 59.80 | 1.547 | <1 |

A portion of the product was calcined at 1000° F. in air for five hours and the following analyses were obtained.

| | |
|---|---|
| Wt. percent SiO₂ | 77.3 |
| Wt. percent Al₂O₃ | 15.5 |
| Wt. percent Na | 6.1 |
| SiO₂/Al₂O₃ | 8.5 |

The following adsorption data was obtained for the calcined product.

| | |
|---|---|
| Wt. percent n-Hexane adsorbed | 10.87 |
| Wt. percent cyclohexane adsorbed | 3.60 |
| Wt. percent H₂O adsorbed | 9.15 |

EXAMPLE II

Figure 2:
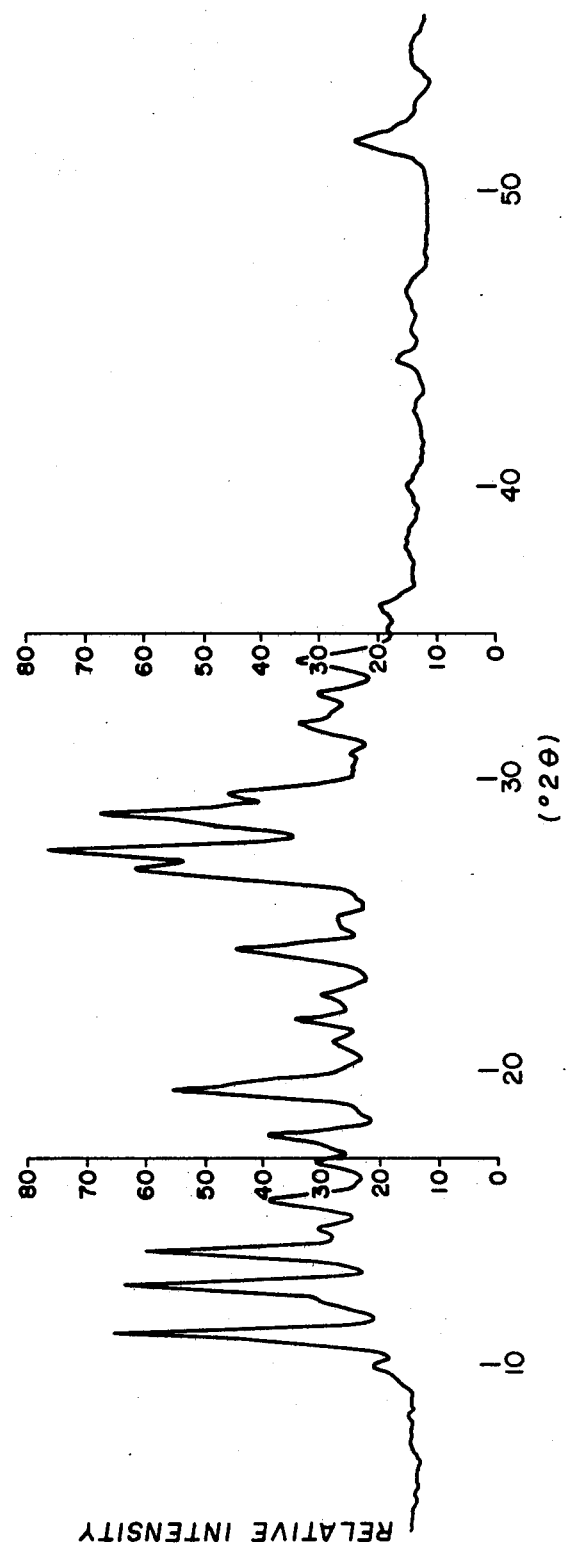
FIG. 2 is an X-ray diffraction pattern of the ZSM-25 product of Example I after being calcined four hours at 500° C.

A thermal stability test was run of a sample of the EXAMPLE I wherein the sample was calcined for four hours at 500° C. in a muffle furnace. Some loss in diffracted intensity and some broadening of lines indicated some lattice distortion with some loss in crystallinity. The X-ray diffraction pattern of the calcined sample is shown in FIG. 2 and TABLE III.

TABLE III

| X-RAY DATA ZSM-25 CALCINED 4 HRS. AT 500° C. | | | | | |
|---|---|---|---|---|---|
| 2θ | d | Relative Intensity | 2θ | d | Relative Intensity |
| 7.18 | 12.3 | 2 | 27.50 | 3.24 | 100 |
| 7.50 | 11.8 | 2 | 28.30 | 3.15 | 22 |
| 8.20 | 10.8 | 2 | 28.80 | 3.10 | 85 |
| 9.50 | 9.31 | 6 | 29.50 | 3.03 | 44 |
| 9.90 | 8.93 | 13 | 29.90 | 2.99 | 6 |
| 10.98 | 8.06 | 96 | 30.40 | 2.94 | 6 |
| 11.95 | 7.41 | 13 | 30.82 | 2.90 | 6 |
| 12.60 | 7.03 | 87 | 31.60 | 2.83 | 6 |
| 13.78 | 6.43 | 80 | 31.90 | 2.80 | 20 |
| 14.20 | 6.24 | 11 | 32.30 | 2.77 | 13 |
| 14.60 | 6.07 | 22 | 32.90 | 2.72 | 20 |
| 15.38 | 5.76 | 22 | 33.70 | 2.66 | 9 |
| 15.70 | 5.64 | 24 | 34.10 | 2.63 | 28 |
| 16.20 | 5.47 | 6 | 34.60 | 2.59 | 4 |
| 16.88 | 5.25 | 22 | 35.22 | 2.55 | 2 |
| 17.35 | 5.11 | 11 | 35.90 | 2.50 | 6 |
| 17.78 | 4.99 | 35 | 36.20 | 2.48 | 4 |
| 18.60 | 4.77 | 6 | 37.90 | 2.37 | 3 |
| 19.25 | 4.61 | 59 | 38.30 | 2.35 | 5 |
| 19.70 | 4.51 | 21 | 38.80 | 2.32 | 3 |
| 20.10 | 4.42 | 6 | 40.10 | 2.25 | 3 |
| 20.50 | 4.33 | 4 | 42.60 | 2.12 | 3 |
| 20.97 | 4.24 | 11 | 43.00 | 2.10 | 2 |
| 21.75 | 4.09 | 22 | 44.25 | 2.05 | 6 |
| 22.17 | 4.01 | 7 | 44.58 | 2.03 | 6 |
| 22.62 | 3.93 | 13 | 45.40 | 1.998 | 4 |
| 23.60 | 3.77 | 7 | 46.10 | 1.969 | 4 |
| 24.15 | 3.69 | 43 | 46.70 | 1.945 | 6 |
| 24.85 | 3.58 | 9 | 47.20 | 1.926 | 4 |
| 25.25 | 3.53 | 9 | 51.70 | 1.768 | 24 |
| 26.50 | 3.36 | 17 | 52.30 | 1.749 | 9 |
| 26.90 | 3.31 | 68 | 52.90 | 1.731 | 6 |

EXAMPLE III

A sample of the ZSM-25 zeolite was subjected to an ammonium chloride base exchange reducing the Na level from an initial value of 6.1 weight percent to a final value of 0.2 weight percent. A sample of this base exchanged ZSM-25 zeolite was evaluated for hydrocarbon cracking activity in the n-Hexane cracking test (alpha test). The test results indicate a cracking activity about 23 times greater than a standard silica-alumina catalyst.

EXAMPLE IV

An oligomerization test was run to illustrate the activity of the base-exchanged (0.2 wt. percent Na) ZSM-25 for hydrocarbon conversion at 700° F. The ZSM-25 sample converted 11.6 weight percent propylene to propylene oligomers.

The alpha test was carried out as follows. n-Hexane diluted with helium was passed over a 1.0 cc. sample of the catalyst at a liquid hourly space velocity = 1 and at 900° F. The conversion of hexane to cracked products at 5 minutes on stream was equal to 22.7%. This calculates to a relative cracking activity (α value) of 22.9.

The oligomerization test was carried out as follows. Propylene was charged at the rate of 16.66 cc/min. (1000 cc/hr.) over a 0.259 g. (0.67 cc.) sample of the catalyst at 700° F. for a two-hour period. A liquid balance was made during the second hour on stream. On the basis of recovered hydrocarbons 14.4% of the propylene was converted. Of this, 83.0% was converted to C₄+ and 57.1% to C₅+ hydrocarbons.

What is claimed is:

1. A crystalline zeolite having a composition in the anhydrous form, expressed in terms of mole ratios of oxides as follows:

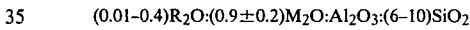

$(0.01-0.4)R_2O:(0.9\pm 0.2)M_2O:Al_2O_3:(6-10)SiO_2$ wherein R is an organic nitrogen-containing cation and M is an alkali metal cation, said zeolite being characterized by an X-ray powder diffraction pattern as set forth in TABLE I of the specification.

2. The crystalline zeolite of claim 1 wherein R is an organic nitrogen-containing cation containing at least one alkyl or aryl group containing from one to seven carbon atoms.

3. The zeolite of claim 2 wherein R contains at least on ethyl group.

4. The zeolite of claim 3 wherein R is a quatenary ammonium cation containing at least one ethyl group.

5. The zeolite of claim 4 wherein R is a tetraethylammonium cation.

6. The zeolite of claim 5 wherein R is derived from tetraethylammonium bromide and M is sodium.

7. A zeolite resulting from the thermal treatment or ion exchange treatment, or a combination thereof, of the zeolite of claim 1, wherein said ion exchange treatment is carried out with hydrogen, ammonium, or metal ions of Groups IB through VIII of the Periodic Table.

8. A zeolite resulting from the thermal treatment or ion exchange treatment, or a combination thereof, of the zeolite of claim 2, wherein said ion exchange treatment is carried out with hydrogen, ammonium, or metal ions of Groups IB through VIII of the Periodic Table.

9. A zeolite resulting from the thermal treatment or ion exchange treatment, or a combination thereof, of the zeolite of claim 3, wherein said ion exchange treatment is carried out with hydrogen, ammonium, or metal ions of Groups IB through VIII of the Periodic Table.

10. A zeolite resulting from the thermal treatment or ion exchange treatment, or a combination thereof, of the zeolite of claim 4, wherein said ion exchange treatment is carried out with hydrogen, ammonium, or metal ions of Groups IB through VIII of the Periodic Table.

11. A zeolite resulting from the thermal treatment or ion exchange treatment, or a combination thereof, of the zeolite of claim 5, wherein said ion exchange treatment is carried out with hydrogen, ammonium, or metal ions of Groups IB through VIII of the Periodic Table.

12. A zeolite resulting from the thermal treatment or ion exchange treatment, or a combination thereof, of the zeolite of claim 6, wherein said ion exchange treatment is carried out with hydrogen, ammonium, or metal ions of Groups IB through VIII of the Periodic Table.

13. The crystalline zeolite of claim 1 admixed with a matrix therefor.

14. The crystalline zeolite of claim 13 wherein said matrix is an inorganic oxide.

UNITED STATES PATENT AND TRADEMARK OFFICE
CERTIFICATE OF CORRECTION

PATENT NO. : 4,247,416

DATED : January 27, 1981

INVENTOR(S) : H. G. Doherty, C. J. Plank & E. J. Rosinki

It is certified that error appears in the above-identified patent and that said Letters Patent is hereby corrected as shown below:

Column 7, line 60 "282" should read --810--

Signed and Sealed this

Sixteenth Day of February, 1988

Attest:

DONALD J. QUIGG

*Attesting Officer*  *Commissioner of Patents and Trademarks*